(12) United States Patent
Carola et al.

(10) Patent No.: US 10,660,867 B2
(45) Date of Patent: May 26, 2020

(54) BETA-HYDROXYKETONES AS TOPICAL ACTIVE INGREDIENTS FOR THE PREVENTION OR TREATMENT OF PHOTODERMATOSES

(71) Applicant: Merck Patent GmbH, Darmstadt (DE)

(72) Inventors: Christophe Carola, Bensheim (DE); Lilia Heider, Gernsheim (DE); Marina Lefort, Darmstadt (DE); Hansjuergen Driller, Gross-Umstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/778,747

(22) PCT Filed: Nov. 2, 2016

(86) PCT No.: PCT/EP2016/001815
§ 371 (c)(1),
(2) Date: May 24, 2018

(87) PCT Pub. No.: WO2017/088950
PCT Pub. Date: Jun. 1, 2017

(65) Prior Publication Data
US 2018/0353442 A1    Dec. 13, 2018

(30) Foreign Application Priority Data
Nov. 27, 2015  (EP) ..................... 15196821

(51) Int. Cl.
  *A61K 31/12*  (2006.01)
  *A61P 17/00*  (2006.01)

(52) U.S. Cl.
  CPC .............. *A61K 31/12* (2013.01); *A61P 17/00* (2018.01)

(58) Field of Classification Search
  CPC ................................ A61K 31/12; A61P 17/00
  See application file for complete search history.

(56) References Cited

U.S. PATENT DOCUMENTS 7,906,684 B2    3/2011   Rudolph

FOREIGN PATENT DOCUMENTS

DE      102006019044 A1    10/2007
WO        2013045016 A2     4/2013

OTHER PUBLICATIONS

Medeiros et al. (STL vol. 15, No. 6, Jun. 2010) pp. 1-10, downloaded from the internet on May 2, 2019. http://www.skintherapyletter.com/sunscreen/photodermatoses/ (Year: 2010).*
International Search Report PCT/EP2016/001815 dated Jan. 20, 2017.

(Continued)

*Primary Examiner* — Savitha M Rao
(74) *Attorney, Agent, or Firm* — Millen, White, Zelano and Branigan, P.C.

(57) ABSTRACT

The present invention relates to specific β-hydroxyketones of the formula (I) for use in the prevention and/or treatment of photodermatoses and to the use of specific β-hydroxyketones of the formula (I) as active ingredient in typical compositions for the prevention and/or non-therapeutic treatment of photodermatoses, in particular of polymorphic light eruption.

4 Claims, 1 Drawing Sheet

(56) References Cited

OTHER PUBLICATIONS

K. S. Ravikumar et al: "Diastereoselectivity in the Reduction of Acyclic Carbonyl Compounds with Diisopropoxytitanium(III) Tetrahydroborate", The Journal of Organic Chemistry, vol. 64, No. 16, Aug. 1, 1999 (Aug. 1, 1999), pp. 5841-5844, XP055334721, ISSN: 0022-3263.
Aiguo Hu et al: "Supporting Information for Ru-Catalyzed Asymmetric Hydrogenation of [alpha]-Phthalimide Ketones and 1,3-Diaryl Diketones Using 4,4'-Substituted BINAPs", Organic Letters; vol. 7, No. 3, Jan. 1, 2005 (Jan. 1, 2005), XP055334019.
Fusaro R M et al: "Topical photoprotection for hereditary polymorphic light eruption of American Indians", Journal of the American Academy of Dermatology, Mosby, Inc, US, vol. 24, No. 5, May 1, 1991 (May 1, 1991), pp. 744-746, XP025616630, ISSN: 0190-9622.

\* cited by examiner

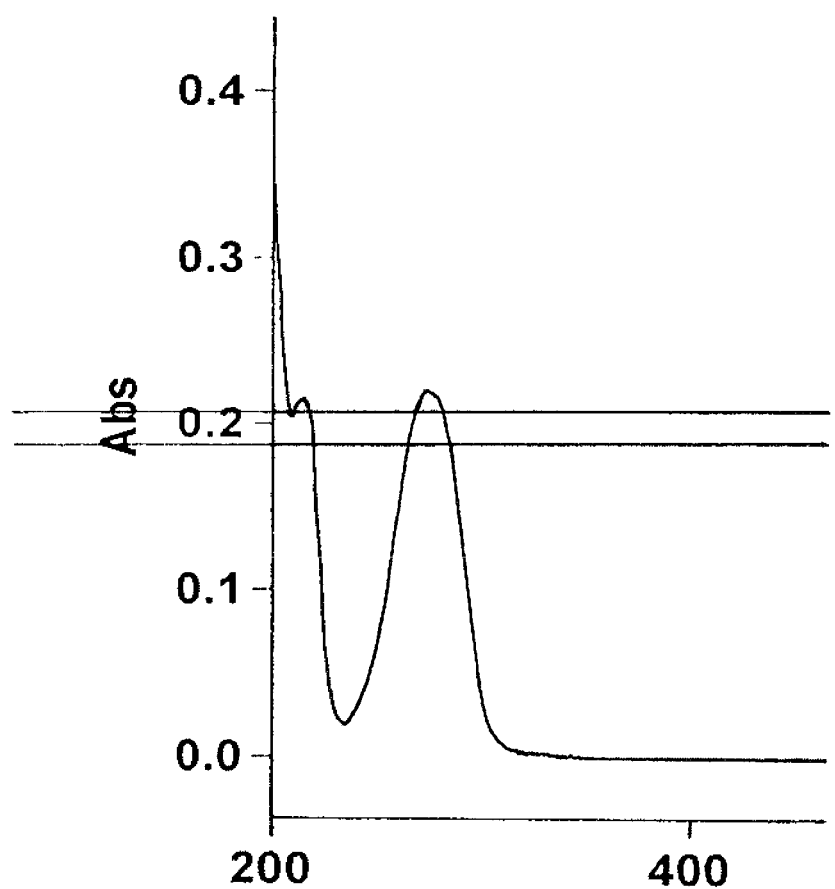

BETA-HYDROXYKETONES AS TOPICAL ACTIVE INGREDIENTS FOR THE PREVENTION OR TREATMENT OF PHOTODERMATOSES

The present invention relates to specific β-hydroxyketones of the formula (I) for use in the prevention and/or treatment of photodermatoses and to the use of specific β-hydroxyketones of the formula (I) as active ingredient in typical compositions for the prevention and/or non-therapeutic treatment of photodermatoses, in particular of polymorphic light eruption.

Photodermatoses are diseases of the skin which arise on exposure to rays, preferably UVA rays, UVB rays and/or visual rays, where these rays may originate from a natural source or artificial sources.

Besides classical sunburn, photodermatoses also include, for example, skin changes owing to a phototoxic reaction or photoallergic reaction to medicaments or, in particular, also polymorphic light eruption.

The presentation of polymorphic light eruption is also called polymorphous light eruption or polymorphic light dermatosis in English-speaking cultures, or provided with the abbreviations PLE, PME, PMLE or PLD. The cause is unknown. However, it is thought that a delayed allergic reaction occurs.

Polymorphic light eruption is a frequently occurring photodermatosis for which it is thought that, in particular, exposure to UVA radiation is responsible. About 11-21% of Northern Europeans are probably affected by these skin appearances.

Polymorphic light eruption usually occurs in spring or early summer after first exposure to the sun. On further exposure to the sun, the episodes usually become weaker as the summer progresses. The skin changes occur, in particular, on the outsides of the upper arms, on the neckline and also on the face. The skin appearances can have a very wide variety of forms (for example reddening, blisters, nodules, weeping skin defects, skin thickening). However, they are usually restricted to one of these forms in any one person. Severe itching is always present.

In order to prevent formation of polymorphic light eruption, it is recommended that direct exposure to the sun be avoided, in particular on days and at times of high light intensity, and the use of sunscreens which contain, in particular, UVA filters.

Suitable sunscreens are described, for example, in A. Fourtanier et al, Photodermatoloty, Photoimmunology & Photomedicine 2008, 24, 164-174.

Besides the UVA filters, sunscreens of this type optionally also contain antioxidants, such as, for example, alpha-glucosylrutin, as described in IM Hadshiew et al, Photodermatoloty, Photoimmunology & Photomedicine 2004, 20(4), 200-4.

PLE is often treated using topical preparations containing corticosteroids or photo(chemo)therapy is carried out.

However, there continues to be a need for active ingredients which are suitable for the prevention and/or treatment of photodermatoses, in particular of polymorphic light eruption.

The object of the invention is therefore to provide active ingredients which enable therapeutic and/or non-therapeutic prevention and/or treatment of photodermatoses, in particular of polymorphic light eruption.

Surprisingly, it has been found that specific β-hydroxyketones of the formula (I) achieve this object.

The invention therefore relates firstly to compounds of the formula (I)

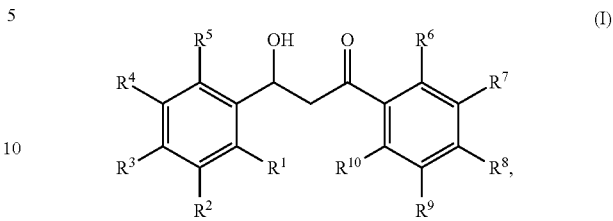

where $R^1$ to $R^{10}$ each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group, for use in the prevention and/or treatment of photodermatoses, preferably for use in the prevention and/or treatment of polymorphic light eruption.

The invention furthermore relates to the use of a compound of the formula (I)

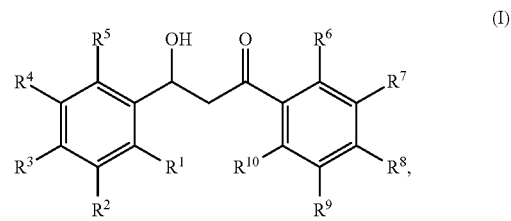

where $R^1$ to $R^{10}$ each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group, as active ingredient in a cosmetic preparation for the non-therapeutic treatment and/or prevention of photodermatosis, in particular for the non-therapeutic treatment and/or prevention of polymorphic light eruption.

The compounds of the formula (I), as described above, are known, inter alia, from WO 2007/121845. The description of WO 2007/121845 encompasses further compounds which do not fall under the formula (I), as described above. In general, all compounds known from WO 2007/121845 are described as antioxidants. As described therein with reference to CD Römpp Lexicon of Chemistry—Version 1.0, Stuttgart/New York: Georg Thieme Verlag 1995, antioxidants are compounds which inhibit or prevent undesired changes in the substances to be protected caused by the action of oxygen, inter alia oxidative processes. They therefore act, in particular, against free radicals, which are formed on the skin by UV radiation.

WO 2007/121845 furthermore describes that specific compounds from the disclosure can also act against a multiplicity of skin diseases, but without explicitly describing the presentation of photodermatosis or in particular of polymorphic light eruption.

The present invention therefore relates to a second medical or non-medical use of known compounds.

The compounds of the formula (I)

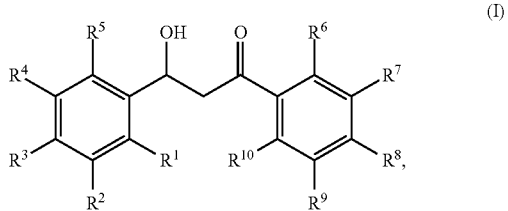

(I)

where $R^1$ to $R^{10}$ each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group, are not UV filters, i.e. they do not exhibit UV absorption. The absorption behaviour for the compound 3-(4-tert-butylphenyl)-3-hydroxy-1-(4-methoxy-phenyl)propan-1-one is depicted in FIG. 1 as representative. At wavelengths of 273 nm and 215.5 nm, the absorption is only 0.22, i.e. the compound 3-(4-tert-butylphenyl)-3-hydroxy-1-(4-methoxyphenyl)propan-1-one does not absorb in the UVA region (UVA, 320-400 nm).

It is furthermore known that compounds of the formula (I), as described above or described as preferred below, additionally have a photostabilising action on the corresponding diketone derivatives. Exposure to sunlight initiates conversion of the compounds of the formula (I) into their diketone derivatives, which are then capable of acting as UVA absorbers. In sunscreen formulations, this thus enables targeted provision of the corresponding UVA absorbers starting from compounds of the formula (I) on exposure to the sun. However, this photoconversion must be accelerated if a significant proportion of UVA filters is to be generated. This is confirmed by the laid-open specifications WO 2011/141111 and DE 102012016960 A1.

As representative of the compounds of the formula (I), the efficacy of 3-(4-tert-butylphenyl)-3-hydroxy-1-(4-methoxy-phenyl)propan-1-one in vivo is confirmed in the experimental part, where the proportion of UVA filter formed by decomposition of 3-(4-tert-butylphenyl)-3-hydroxy-1-(4-methoxy-phenyl)propan-1-one on exposure to UV light under the selected conditions of the study is only 0.1% by weight. Such a proportion of a UVA filter does not effect efficient UVA protection and therefore cannot be responsible for the positive results of the in vivo study and the efficacy against the formation of photodermatosis, in particular polymorphic light eruption.

The compounds of the formula (I) accordingly prevent the occurrence of the presentation of photodermatosis, in particular of polymorphic light eruption. Accordingly, the second medical use or second non-medical use of the compounds of the formula (I) is preferably prevention of photodermatoses, particularly preferably prevention of polymorphic light eruption.

In addition, it is even advantageous that the compounds of the formula (I), as described above and preferably described below, are effective as such can be converted into a UVA filter after decomposition by exposure to sunlight, and thus themselves further support prevention of photodermatosis after their own decomposition by exposure to the sun.

It is furthermore thought that the compounds of the formula (I), as described above or preferably described below, have an inflammation-inhibiting action. This property also supports the therapeutic and non-therapeutic treatment of photodermatosis. The compounds of the formula (I), in particular 3-(4-tert-butylphenyl)-3-hydroxy-1-(4-methoxyphenyl)propan-1-one, inhibit/inhibits activation of the transcription factor NF-κB, which is a key regulator in the expression of many genes which are involved in inflammation, as described in Baeuerle, Cell. 1998, 95(6):729-31.

As described above, the substituents $R^1$ to $R^{10}$ can each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group.

Straight-chain or branched alkyl groups having 1 to 4, 1 to 8, 1 to 12 or 1 to 20 C atoms conform to the formula $C_pH_{2p+1}$ where p=1, 2, 3 or 4, or 1, 2, 3, 4, 5, 6, 7 or 8, or 1, 2, 3, 4, 5, 6, 7, 8, 9, 10, 11 or 12, or 1, 2, 3, 4, 5, 6, 7, 8, 9, 10, 11, 12, 13, 14, 15, 16, 17, 18, 19 or 20, for example methyl, ethyl, i-propyl, propyl, butyl, i-butyl or tert-butyl, pentyl, 1-, 2- or 3-methylbutyl, 1,1-, 1,2- or 2,2-dimethylpropyl, 1-ethylpropyl or hexyl, heptyl, octyl, nonyl, decyl, undecyl, dodecyl, tridecyl, tetradecyl, pentadecyl, hexadecyl, heptadecyl, octadecyl, nonadecyl or eicosyl.

If an alkyl group is not designated in greater detail, it is a straight-chain alkyl group.

Straight-chain or branched alkoxy groups having 1 to 4, 1 to 8, 1 to 12 or 1 to 20 C atoms conform to the formula $OC_pH_{2p+1}$ where p=1, 2, 3 or 4, or 1, 2, 3, 4, 5, 6, 7 or 8, or 1, 2, 3, 4, 5, 6, 7, 8, 9, 10, 11 or 12, or 1, 2, 3, 4, 5, 6, 7, 8, 9, 10, 11, 12, 13, 14, 15, 16, 17, 18, 19 or 20, for example methoxy, ethyoxy, i-propyloxy, propyloxy, butyloxy, i-butyloxy or tert-butyloxy, pentyloxy, 1-, 2- or 3-methylbutyloxy, 1,1-, 1,2- or 2,2-dimethylpropyloxy, 1-ethylpropyloxy or hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy or eicosyloxy.

Straight-chain or branched alkoxy groups having 1 to 4, 1 to 8, 1 to 12 or 1 to 20 C atoms conform to the formula $OC_pH_{2p+1}$ where p=1, 2, 3 or 4, or 1, 2, 3, 4, 5, 6, 7 or 8, or 1, 2, 3, 4, 5, 6, 7, 8, 9, 10, 11 or 12, or 1, 2, 3, 4, 5, 6, 7, 8, 9, 10, 11, 12, 13, 14, 15, 16, 17, 18, 19 or 20, for example methoxy, ethyoxy, i-propyloxy, propyloxy, butyloxy, i-butyloxy or tert-butyloxy, pentyloxy, 1-, 2- or 3-methylbutyloxy, 1,1-, 1,2- or 2,2-dimethylpropyloxy, 1-ethylpropyloxy or hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy or eicosyloxy.

Straight-chain or branched dialkylamino groups having 1 to 4, 1 to 8, 1 to 12 or 1 to 20 C atoms conform to the formula $N(C_pH_{2p+1})_2$ where p in each case, independently of one another, 1, 2, 3 or 4, or 1, 2, 3, 4, 5, 6, 7 or 8, or 1, 2, 3, 4, 5, 6, 7, 8, 9, 10, 11 or 12, or 1, 2, 3, 4, 5, 6, 7, 8, 9, 10, 11, 12, 13, 14, 15, 16, 17, 18, 19 or 20, for example dimethylamino, methylethylamino, diethylamino, di(i-propyl)amino, methylpropylamino, ethylpropylamino, dipropylamino, methylbutylamino, ethylbutylamino, propylbutylamino, dibutylamino, di(i-butyl)amino or di(tert-butyl)amino, dipentylamino, di(1-, 2- or 3-methyl)butylamino, di(1,1-, 1,2- or 2,2-dimethylpropyl)amino, di(1-ethylpropyl)amino or dihexylamino, diheptylamino, dioctylamino, dinonylamino, didecylamino, diundecylamino, didodecylamino, ditridecylamino, ditetradecylamino, dipentadecylamino, dihexadecylaminoy, diheptadecylamino, dioctadecylamino, dinonadecylamino or dieicosylamino.

In the substituents $R^1$ to $R^{10}$, the alkyl groups are in each case, independently of one another, straight-chain or branched and preferably have 1 to 12 C atoms, particularly preferably 1 to 4 C atoms.

In the substituents $R^1$ to $R^{10}$, the alkoxy groups are in each case, independently of one another, straight-chain or branched and preferably have 1 to 12 C atoms, particularly preferably 1 to 4 C atoms.

In the substituents $R^1$ to $R^{10}$ the diaminoalkyl groups are in each case, independently of one another, straight-chain or branched and preferably have 1 to 12 C atoms, particularly preferably 1 to 4 C atoms.

Preferred compounds of the formula (I) are compounds in which $R^1$, $R^2$, $R^4$, $R^5$, $R^6$, $R^7$, $R^9$ and $R^{10}$ denote H and $R^3$ and $R^8$ each, independently of one another, denote a straight-chain or branched $C_1$- to $C_{12}$-alkyl group or a straight-chain or branched $C_1$- to $C_{12}$-alkoxy group.

Particularly preferred compounds of the formula (I) are compounds in which $R^1$, $R^2$, $R^4$, $R^5$, $R^6$, $R^7$, $R^9$ and $R^{10}$ denote H and $R^3$ and $R^8$ each, independently of one another, denote a straight-chain or branched $C_1$- to $C_4$-alkyl group or a straight-chain or branched $C_1$- to $C_4$-alkoxy group.

Very particularly preferred compounds of the formula (I) are 3-(4-tert-butyl-phenyl)-3-hydroxy-1-(4-methoxyphenyl) propan-1-one, 1-(4-tert-butyl-phenyl)-3-hydroxy-3-(4-methoxyphenyl)propan-1-one or a mixture thereof. The compound 3-(4-tert-butylphenyl)-3-hydroxy-1-(4-methoxyphenyl)-propan-1-one is very particularly preferably used in accordance with the invention.

The invention therefore furthermore relates to compounds of the formula (I), as described above, in which $R^1$, $R^2$, $R^4$, $R^5$, $R^6$, $R^7$, $R^9$ and $R^{10}$ denote H and $R^3$ and $R^8$ each, independently of one another, denote a straight-chain or branched $C_1$- to $C_{12}$-alkyl group or a straight-chain or branched $C_1$- to $C_{12}$-alkoxy group, for use in the prevention and/or treatment of photodermatoses, in particular in the prevention of polymorphic light eruption.

The invention therefore furthermore relates to compounds of the formula (I), as described above, in which $R^1$, $R^2$, $R^4$, $R^5$, $R^6$, $R^7$, $R^9$ and $R^{10}$ denote H and $R^3$ and $R^8$ each, independently of one another, denote a straight-chain or branched $C_1$- to $C_4$-alkyl group or a straight-chain or branched $C_1$- to $C_4$-alkoxy group, for use in the prevention and/or treatment of photodermatoses, in particular in the prevention of polymorphic light eruption.

The invention therefore furthermore relates to the compounds 3-(4-tert-butylphenyl)-3-hydroxy-1-(4-methoxyphenyl)propan-1-one, 1-(4-tert-butyl-phenyl)-3-hydroxy-3-(4-methoxyphenyl)propan-1-one or a mixture thereof, for use in the prevention and/or treatment of photodermatoses, in particular in the prevention of polymorphic light eruption.

The invention therefore furthermore relates to the use of compounds of the formula (I) as active ingredient in a cosmetic preparation for the non-therapeutic treatment and/or prevention of photodermatosis, in particular for the prevention of polymorphic light eruption, where the substituents $R^1$, $R^2$, $R^4$, $R^5$, $R^6$, $R^7$, $R^9$ and $R^{10}$ of the compound of the formula (I) denote H and $R^3$ and $R^8$ each, independently of one another, denote a straight-chain or branched $C_1$- to $C_{12}$-alkyl group or a straight-chain or branched $C_1$- to $C_{12}$-alkoxy group.

The invention therefore furthermore relates to the use of compounds of the formula (I) as active ingredient in a cosmetic preparation for the non-therapeutic treatment and/ or prevention of photodermatosis, in particular for the prevention of polymorphic light eruption, where the substituents $R^1$, $R^2$, $R^4$, $R^5$, $R^6$, $R^7$, $R^9$ and $R^{10}$ of the compound of the formula (I) denote H and $R^3$ and $R^8$ each, independently of one another, denote a straight-chain or branched $C_1$- to $C_4$-alkyl group or a straight-chain or branched $C_1$- to $C_4$-alkoxy group.

The invention therefore furthermore relates to the use of the compounds 3-(4-tert-butylphenyl)-3-hydroxy-1-(4-methoxyphenyl)propan-1-one, 1-(4-tert-butylphenyl)-3-hydroxy-3-(4-methoxyphenyl)propan-1-one or a mixture thereof as active ingredient(s) in a cosmetic preparation for the non-therapeutic treatment and/or prevention of photodermatosis, in particular for the prevention of polymorphic light eruption.

The invention is furthermore directed to a non-therapeutic method for the prevention of photodermatoses, characterised in that a cosmetic preparation which comprises at least one compound of the formula (I), as described above or described as preferred, is applied to the skin.

The invention is furthermore directed to a non-therapeutic method for the prevention of polymorphic light eruption, characterised in that a cosmetic preparation which comprises at least one compound of the formula (I), as described above or described as preferred, is applied to the skin.

The invention is furthermore directed to a non-therapeutic method for the prevention of polymorphic light eruption, characterised in that a cosmetic preparation which comprises 3-(4-tert-butylphenyl)-3-hydroxy-1-(4-methoxyphenyl)propan-1-one, 1-(4-tert-butylphenyl)-3-hydroxy-3-(4-methoxyphenyl)propan-1-one or a mixture thereof is applied to the skin.

The type of cosmetic and pharmaceutical preparation comprising at least one compound of the formula (I), as described above or preferably described, is not restricted here.

Suitable preparations are known, for example, from WO 2007/121845, WO 2011/141111 and DE 102012016960 A1.

In the second non-medical use or in the second medical use, the compounds of the formula (I), as described above or preferably described, are preferably incorporated into the corresponding preparations in an amount of 1 to 10 percent by weight, preferably 2-5% by weight.

Combination of the compounds of the formula (I), as described above or described as preferred, with other active ingredients which are likewise preventative or suitable as treatment for photodermatoses, preferably for polymorphic light eruption, is advantageous.

Particularly suitable active ingredients for combination are, for example, 1-(4-methoxyphenyl)-3-(4-tert-butylphenyl)-1,3-propanedione (Eusolex® 9020 (Merck)), Escamule (Mexoryl® SX (Chimex), broad-band filters, such as uncoated or coated titanium dioxides, zinc oxides or particulate filters, such as Tinosorb® S, Tinosorb® M or Tris Biphenyl Triazine (TBPT), marketed by BASF, optionally in combination with suitable antioxidants, such as, for example, α-glucosylrutin, isoquercetin or bis(2-ethylhexyl) 2-(4-hydroxy-3,5-dimethoxybenzy)malonate (RonaCare® AP (Merck)).

The following working examples are intended to explain the invention without limiting it. The invention can be carried out correspondingly throughout the range claimed. Starting from the example, possible variants can also be derived. Thus, the features and conditions of the reactions described in the example can also be applied to other reactions which are not described in detail, but fall within the scope of protection of the claims.

EXAMPLES

The compound 3-(4-tert-butylphenyl)-3-hydroxy-1-(4-methoxyphenyl)-propan-1-one (abbreviated to compound A) is prepared analogously to the description of DE 102010055084 A1, Example 1.

In the in vivo study described below, the following O/W emulsion is used:

| Ingredients | INCI | [% by wt.] | [g] |
|---|---|---|---|
| A | | | |
| Compound A | Methoxy Monobenzoylmethane | 2.0 | 20.0 |
| Montanov 202 | Arachidyl Alcohol, Behenyl Alcohol | 3.0 | 30.0 |
| Lanol 99 | Isononyl Isononanoate | 2.0 | 20.0 |
| Miglyol 812N | Caprylylic/Capric Triglyceride | 2.0 | 20.0 |
| Cetiol CC | Dicaprylyl Carbonate | 3.0 | 30.0 |
| Cocoate BG | Butylene Glycol Cocoate | 2.0 | 20.0 |
| B | | | |
| Water, demin. | Aqua (water) | 76.7 | 767.0 |
| 1,2-Propanediol | Propylene Glycol | 6.0 | 60.0 |
| Phospholipon 90 G | Phosphatidyl Choline | 0.3 | 3.0 |
| C | | | |
| Simulgel NS | Hydroxyethyl Acrylate/Sodium, Squalane, Polysorbate 60, Acryloyldimethyltaurate Copolymer | 2.β | 20.0 |
| E | | pH 5.9 | |
| Euxyl PE9010 | Phenoxyethanol, Ethylhexylglycerin | 1.0 | 10.0 |
| Citric acid | Aqua(water) Citric Acid | 1 drop | |

A comparative study with positive control is carried out on 6 test subjects with known PLE syndrome. The study was carried out in Germany in April over a period of 5 days. The positive control was untreated, irradiated skin. The irradiation was carried out with 100% UVA light in a sub-erythemal dose, which was determined individually. The preparation was applied daily to half of the décolletage (2 mg/cm$^2$).

The measurements were carried out twice daily, 10 min. after application of the preparation and immediately after irradiation.

Under the conditions of the in vivo study, conversion of compound A into the UVA filter avobenzone in an amount which could exert an influence on the skin appearances of the test subjects can be excluded.

This can be stated because if a 2% solution of compound A in Cosmacol® ELI (C12-13 alkyl lactate) is irradiated with UVA/UVB light (20/1) in a dose of 5 MED (corresponding to 250 kJ/m$^2$), 0.1% of avobenzone is formed by conversion.

Under the conditions of the in vivo experiment, a UVA dose of 20 J/cm$^2$ (corresponding to 200 kJ/m$^2$) is irradiated, i.e. even less than 0.1% of avobenzone will form by conversion under these conditions.

Table 1 shows skin reactions on UVA irradiation in the case of untreated skin:

| | | Test subject | | | | | |
|---|---|---|---|---|---|---|---|
| Day | Irradiation | 1 | 2 | 3 | 4 | 5 | 6 |
| 1 | before | 0 | 0 | 0 | 0 | 0 | 0 |
| | after | 0 | 0 | 0 | 0 | 0 | 0 |
| 2 | before | 0 | ± | ± | 0 | 0 | 0 |
| | after | itching | ± | ± | 0 | 0 | 0 |
| 3 | before | ± | ± | ± | ± | 0 | ± |
| | after | ± | ± | ± | ± | 0 | + |
| 4 | before | ± | ± | ± | ± | 0 | + |
| | after | + | + | ± | + | + | + |
| 5 | before | + | + | + | + | + | + |
| | after | + | + | + | + | + | + |

Table 2 shows skin reactions on UVA irradiation in the case of treated skin:

| | | Test subject | | | | | |
|---|---|---|---|---|---|---|---|
| Day | Irradiation | 1 | 2 | 3 | 4 | 5 | 6 |
| 1 | before | 0 | 0 | 0 | 0 | 0 | 0 |
| | after | 0 | 0 | 0 | 0 | 0 | 0 |
| 2 | before | 0 | 0 | 0 | 0 | 0 | 0 |
| | after | 0 | 0 | 0 | 0 | 0 | 0 |
| 3 | before | 0 | 0 | 0 | 0 | 0 | ± |
| | after | 0 | 0 | 0 | 0 | 0 | ± |
| 4 | before | ± | 0 | 0 | 0 | 0 | ± |
| | after | ± | 0 | 0 | 0 | 0 | ± |
| 5 | before | ± | 0 | 0 | 0 | 0 | ± |
| | after | ± | 0 | 0 | 0 | 0 | ± |

0 denotes no reaction
± denotes weak reaction
+ denotes clear reaction
++ denotes strong reaction
+++ denotes very strong reaction Results:

In the case of all test subjects, skin manifestations which have the presentation of polymorphic light eruption appeared on untreated skin. In case of 4 test subjects, no polymorphic light eruption was observed on treated skin. Only in the case of 2 test subjects was a weak reaction observed. The results therefore confirm that compound A as such suppresses or significantly reduces the manifestations of polymorphic light eruption on irradiation.

INDEX OF THE FIGURES

FIG. 1 shows the absorption spectrum of the compound 3-(4-tert-butyl-phenyl)-3-hydroxy-1-(4-methoxyphenyl) propan-1-one.

The invention claimed is:

1. A method for the prevention or treatment of polymorphic light eruption, comprising administering to the skin of a host in need thereof an effective amount of a compound that is 3-(4-tert-butylphenyl)-3-hydroxy-1-(4-methoxyphenyl)propan-1-one,1-(4-tert-butylphenyl)-3-hydroxy-3-(4-methoxyphenyl)propan-1one or a mixture thereof.

2. The method according to claim 1, comprising prevention of polymorphic light eruption.

3. The method according to claim 1, comprising treatment of polymorphic light eruption.

4. The method according to claim 1, comprising administering 3-(4-tert-butylphenyl)-3-hydroxy-1-(4-methoxyphenyl)-propan-1-one.

* * * * *